(12) United States Patent
Bodenhamer

(10) Patent No.: US 7,226,753 B2
(45) Date of Patent: Jun. 5, 2007

(54) DISPLACEMENT ASSAY FOR SELECTIVE BIOLOGICAL MATERIAL DETECTION

(75) Inventor: William T. Bodenhamer, Jupiter, FL (US)

(73) Assignee: Toxin Alert, Inc., Ontario (CA)

( * ) Notice: Subject to any disclaimer, the term of this patent is extended or adjusted under 35 U.S.C. 154(b) by 103 days.

(21) Appl. No.: 10/767,464

(22) Filed: Jan. 28, 2004

(65) Prior Publication Data

US 2004/0259178 A1    Dec. 23, 2004

Related U.S. Application Data

(60) Provisional application No. 60/443,299, filed on Jan. 28, 2003.

(51) Int. Cl.
*G01N 33/00* (2006.01)
(52) U.S. Cl. .................. 435/7.93; 435/4; 435/7.9; 435/7.92; 435/28; 436/518; 436/531; 436/535
(58) Field of Classification Search .................. None
See application file for complete search history.

(56) References Cited

U.S. PATENT DOCUMENTS

| | | | | |
|---|---|---|---|---|
| 4,434,236 A | * | 2/1984 | Freytag | 435/5 |
| 4,895,809 A | * | 1/1990 | Schlabach et al. | 436/518 |
| 5,354,654 A | * | 10/1994 | Ligler et al. | 435/5 |

* cited by examiner

*Primary Examiner*—Christopher L. Chin
(74) *Attorney, Agent, or Firm*—McHale & Slavin, P.A.

(57) ABSTRACT

The present invention relates to displacement assay type bioassay materials useful for the detection of toxic substances and, more particularly, to packaging materials for food and other products, along with methods for their manufacture and use. The invention provides a unique composite material capable of detecting and identifying multiple biological materials within a single package. The biological material identification system is designed for incorporation into existing types of flexible packaging material such as polyvinylchloride or polyolefin films, and its introduction into the existing packaging infrastructure will require little or no change to present systems or procedures.

3 Claims, 4 Drawing Sheets

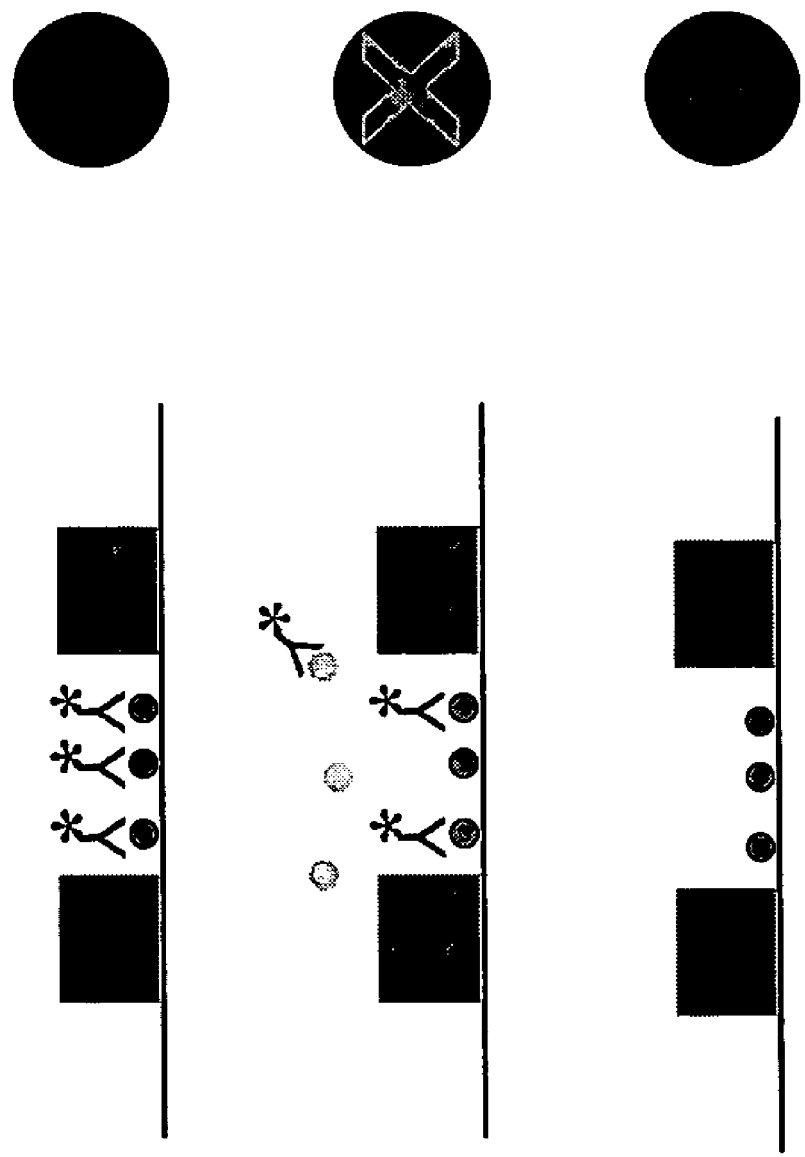

DISPLACEMENT ASSAY FOR SELECTIVE BIOLOGICAL MATERIAL DETECTION

REFERENCE TO RELATED APPLICATIONS

This application seeks benefit of the filing date of U.S. Provisional Application 60/443,299, filed Jan. 28, 2003, the contents of which is herein incorporated by reference in its entirety.

FIELD OF THE INVENTION

This invention relates to the detection of pathogenic microorganisms, or biological materials, and more particularly relates to a composite bioassay material useful for the detection of particular toxic substances, its method of manufacture and method of use, wherein the composite material is particularly useful for food packaging and the like, and is capable of simultaneously detecting and identifying a multiplicity of such biological materials.

BACKGROUND OF THE INVENTION

Although considerable effort and expense have been put forth in an effort to control food borne pathogenic microorganisms, there nevertheless exist significant safety problems in the supply of packaged food. For example, numerous outbreaks of food poisoning brought about by foodstuffs contaminated with strains of the *E-Coli, Campylobacter, Listeria, Cyclospora* and *Salmonella* microorganisms have caused illness and even death, not to mention a tremendous loss of revenue for food producers. These and other microorganisms can inadvertently taint food, even when reasonably careful food handling procedures are followed. The possibility of accidental contamination, for example by temperature abuse, in and of itself, is enough to warrant incorporation of safe and effective biological material diagnosis and detection procedures. Further complicating the situation is the very real possibility that a terrorist organization might target either the food or water supply of a municipality or even a nation itself, by attempting to include a pathogenic microorganism or toxic contaminant capable of causing widespread illness or even death. If, by accident or design, the food supply of a particular population were to be contaminated, it is not only imperative that the population be alerted to the contamination, but it is further necessary that the particular contaminant be quickly and precisely pinpointed so that appropriate countermeasures may be taken.

Thus, if it were possible to readily substitute standard packaging materials with a flexible material capable of
1) quickly and easily detecting the presence, and
2) indicating the particular identity of a variety of pathogenic biological materials, a long felt need would be satisfied.

DESCRIPTION OF THE PRIOR ART

The Berkeley Lab Research News of Dec. 10, 1996, in an article entitle "New Sensor Provides First Instant Test for Toxic *E. Coli* Organism" reports on the work of Stevens and Cheng to develop sensors capable of detecting *E. Coli* strain 0157:H7. A color change from blue to red instantaneously signals the presence of the virulent *E. Coli* 0157:H7 microorganism. Prior art required test sampling and a 24 hour culture period in order to determine the presence of the *E. Coli* microorganism, requiring the use of a variety of diagnostic tools including dyes and microscopes. An alternative technique, involving the use of polymerase chain reaction technology, multiplies the amount of DNA present in a sample until it reaches a detectable level. This test requires several hours before results can be obtained. The Berkeley sensor is inexpensive and may be placed on a variety of materials such as plastic, paper, or glass, e.g. within a bottle cap or container lid. Multiple copies of a single molecule are fabricated into a thin film which has a two part composite structure. The surface binds the biological material while the backbone underlying the surface is the color-changing signaling system.

The Berkeley researchers do not teach the concept of incorporating any means for self-detection within food packaging, nor do they contemplate the inclusion of multiple means capable of both detecting and identifying the source of pathogenic contamination to a technically untrained end user, e.g. the food purchaser or consumer.

Wang et al, in an article entitled "An immune-capturing and concentrating procedure for *Escherichia coli* 0157:H7 and its detection by epifluorescence microscopy" published in Food Microbiology, 1998, Vol. 15 discloses the capture of *E. coli* on a polyvinylchloride sheet coated with polyclonal anti-*E. coli* 0157:H7 antibody and stained with fluorescein-labeled anti-*E. coli* 0157:H7. After being scraped from the PVC surface, the cells were subjected to epifluorescence microscopy for determining presence and concentration. The reference fails to teach or suggest the concept of incorporating any means for self-detection within food packaging, nor does it contemplate the inclusion of multiple means capable of both detecting and identifying the source of pathogenic contamination to a technically untrained end user, e.g. the food purchaser or consumer, and especially fails to disclose such detection without the use of specialized detection techniques and equipment.

U.S. Pat. No. 5,776,672 discloses a single stranded nucleic acid probe having a base sequence complementary to the gene to be detected which is immobilized onto the surface of an optical fiber and then reacted with the gene sample denatured to a single stranded form. The nucleic acid probe, hybridized with the gene is detected by electrochemical or optical detection methodology. In contrast to the instantly disclosed invention, this reference does not suggest the immobilization of the probe onto a flexible polyvinylchloride or polyolefin film, nor does it suggest the utilization of gelcoats having varying porosities to act as a control or limiting agent with respect to the migration of antibodies or microbial material through the bioassay test material, or to serve as a medium for enhancement of the growth of the microbial material.

U.S. Pat. No. 5,756,291 discloses a method of identifying oligomer sequences. The method generates aptamers which are capable of binding to serum factors and all surface molecules. Complexation of the target molecules with a mixture of nucleotides occurs under conditions wherein a complex is formed with the specific binding sequences but not with the other members of the oligonucleotide mixture. The reference fails to suggest the immobilization of the aptamers upon a flexible polyvinylchloride or polyolefin base material, nor does it suggest the use of a protective gelcoat layer which acts as a means to selectively control the migration of antibodies and antigens, or to serve as a medium for enhancement of the growth of microbial material.

SUMMARY OF THE INVENTION

The present invention relates to a displacement assay particularly adapted for use in packaging materials for food and other products, along with methods for their manufacture and use. The presence of undesirable biological materials in the packaged material is readily ascertained by the consumer, merchant, regulator, etc. under ordinary conditions and without the use of special equipment. A multiplicity of biological materials threaten our food supply. The present invention provides a unique composite material capable of detecting and identifying multiple biological materials within a single package. The biological material identification system is designed for incorporation into existing types of flexible packaging material such as polyvinylchloride and polyolefin films, and its introduction into the existing packaging infrastructure will require little or no change to present systems or procedures. Thus, the widespread inclusion of the biological material detecting system of the instant invention will be both efficient and economical.

In one embodiment of the invention the biological material detecting system prints a pattern containing several antibodies or aptamers, derived from plant or animal origins, onto a packaging material which is usually a type of polymeric film, preferably a polyvinylchloride or polyolefin film and most preferably a polyethylene film which has undergone a surface treatment, e.g. corona discharge to enhance the film's ability to immobilize the antibodies upon its surface. The agents are protected by a special abrasion resistant gel coat in which the porosity is tailored to control the ability of certain antibodies, toxic substances, etc. to migrate therethrough. Each antibody is specific to a particular biological material and is printed having a distinctive icon shape. The detection system may contain any number of antibodies capable of detecting a variety of common toxic food microbes; although any number of microbes may be identified via the inventive concept taught herein, for the purpose of this description, the microbes of interest will be limited to *E. Coli, Salmonella, Listeria* and *Cyclospora*.

An important feature of the biological material detection system is its all-encompassing presence around and upon the product being packaged. Since the biological material detecting system is designed as an integral part of the packaging material and covers all surfaces as utilized, there is no part of the packaged product which can be exposed to undetected microbes. In the past, the use of single location or in situ detectors have left a majority of the area around and upon the packaged product exposed to undetected microbes. This greatly increased the chance that a spoiled or tainted product might be inadvertently consumed before the toxic agent had spread to the location of the in situ detector. The biological material detection system of the present invention avoids this problem by providing a plurality of individual detectors per unit area which are effective to insure positive detection of any pathogenic microorganisms within the product being tested. In order to be effective a particular degree of sensitivity is required, e.g. the detecting system must be capable of positively identifying one microbial cell in a 25 gram meat sample In a preferred embodiment, four detectors per square inch of packaging material surface have been utilized, and in a most preferred embodiment nine or more detectors per square inch are incorporated upon the film's surface.

By use of the biological material detection system of the present invention a packager or processor can independently determine the multiplicity and identity of those biological materials against which the packaged product is to be protected. Although it is envisioned that the large majority of biological material detection treated packaging will be generic to approximately four of the most common microbes, the system will nevertheless allow each user to customize the protection offered to the public.

The biological material detecting system will not merely detect the presence of biological materials, it will also identify the particular biological materials located in a packaged product. This unique feature allows for the immediate identification of each particular biological material present since the antibodies are specific to a detector having a definitive icon shape or other identifying characteristic. Although the end use consumer is primarily interested in whether a food product is, or is not, contaminated per se, the ability to detect and identify the particular biological material immediately is of immeasurable value to merchants, processors, regulators and health officials. The ability to immediately identify a toxic material will lead to greatly reduced response times to health threats that might be caused by the biological material and will also enhance the ability for authorities to locate the source of the problem. The biological material detecting system of the present invention exhibits an active shelf life in excess of 1 year under normal operating conditions. This enhances the use of a biological material detection system on products which are intended to be stored for long periods of time. If these products are stored so as to be ready for immediate use in some time of emergency, then it is extremely beneficial to definitely be able to determine the safety of the product at the time that it is to be used.

One particularly important feature of the biological material detecting system of the instant invention is its ability to quantitatively sensitize the reagents so as to visually identify only those biological materials which have reached a predetermined concentration or threshold level which is deemed to be harmful to humans.

For example, almost all poultry meat contain traces of the *salmonella* bacteria. In most cases, the *salmonella* levels have not reached a harmful level of concentration. The biological material detecting reagents are designed to visually report only those instances where the level of concentration of biological materials are deemed harmful by health regulatory bodies.

The method of production of the biological material detecting system is designed to be easily incorporated within the packaging infrastructure of existing systems without disruption of the systems or the procedures under which they are operating. The biological material detecting system can be incorporated onto packaging films which are produced by the packager, or those which are supplied by a film manufacturer. The apparatus necessary for applying the biological material detecting system may be easily located at the beginning of any continuous process such as printing or laminating and will operate as an integral part of an existing system.

The biological material detecting system of the instant invention represents an entirely new packaging material which is designed to inform the consumer of the presence of certain biological materials or pathogens present in food stuffs or other materials packaged within the detecting system. The system is designed so that the presence of a biological material is presented to the consumer in a distinct, unmistakable manner which is easily visible to the naked eye.

Recent outbreaks of *E. Coli* and other health hazards have presented serious problems to the general population and have raised concerns regarding the safety of the food supply.

It is an objective of the present invention to provide a biological material detecting system, in the form of a novel displacement assay technology, for protecting the consumer by detecting and unmistakably presenting to the untrained eye visual icons on the packaging material which signify the presence of a number of pathogens in the food stuff or other materials which are at a level harmful to humans.

It is another objective of the instant invention to provide a bioassay material wherein an antigen detecting antibody system is immobilized upon the surface of a flexible polyolefin film.

It is still another objective of the instant invention to provide a bioassay material wherein an antigen detecting antibody system is immobilized upon the surface of a flexible polyvinylchloride film.

It is a further objective of the invention to provide a biological material detecting system which is so similar in appearance and utilization that its use, in lieu of traditional packaging materials, is not apparent to the food processor or other packagers.

A still further objective of the present invention is to provide a biological material detecting system which is cost effective when compared to traditional packaging materials.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 4 is an illustration of a displacement assay.

DESCRIPTION OF THE PREFERRED EMBODIMENT(S)

Antibody Displacement Assay Format

With each assay developed for the displacement assay format, the specific antigen could be comprised of different material. For example, the PSEUDOMONAS assay has an oligosaccharide as the specific antigen, the pesticide assays will each have a different small molecule as the specific antigen and other assays could have lipids, proteins, or other biological/chemical substances as the specific antigen.

The differing nature of each specific antigen will pose difficulties with the standardization of the chemistry involved in providing pigment to each assay developed.

The component common to all assays to be developed will be the antibody. By using the antibody as the displaceable material, the pigmentation chemistry can be directly transferable between assays.

It is thus proposed to print the specific antigen, or a facsimile of the specific antigen, on the plastic film and overprint the pigmented antibody. In this way, the pigmented antibody will be displaced by the contaminating test material; indicating a positive response on the plastic film. In accordance with this invention, a "facsimile antigen" is understood to mean any compound which has a controllable affinity for a particular antibody or immunogenic fragment thereof.

Figure 1:
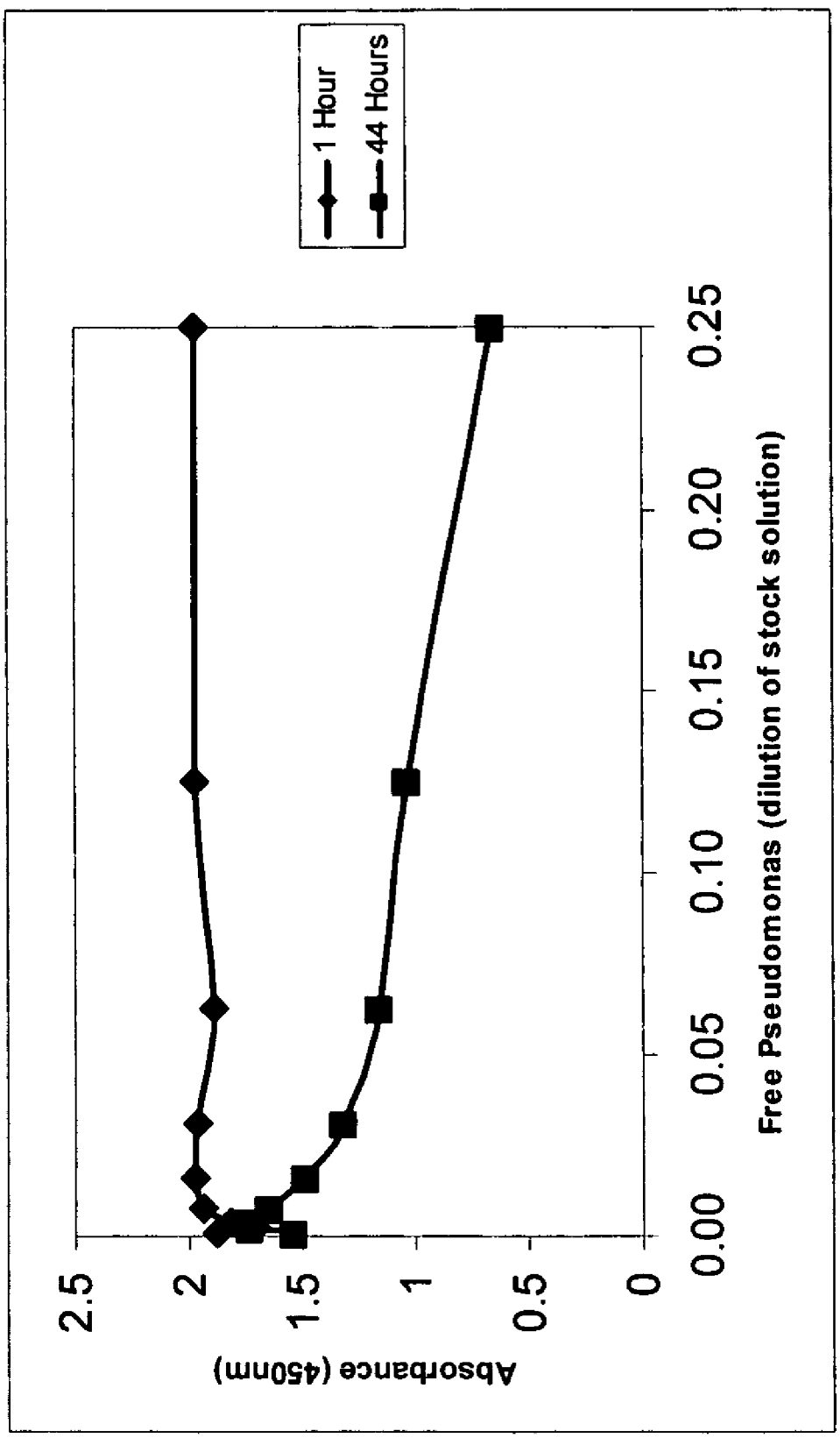
FIG. 1 is a graph which demonstrates the displacement of HRP-conjugated antibody from *Pseudomonas* coated on a polystyrene plate by varied amounts of free *Pseudomonas* in solution.

The graph in FIG. 1 demonstrates the displacement of HRP-conjugated antibody from *Pseudomonas* coated on a polystyrene plate by varied amounts of free *Pseudomonas* in solution.

Process Steps—Proof of Concept

1. Produce Heat-killed Pseudomonas.
2. Coat bottom of an ELISA plate
3. HRP-Ab binds to Pseudomonas.
4. Add free heat-killed Pseudomonas in solution.
5. After 1 & 4 hrs unbound Pseudomonas is washed away.
6. Add tetramethyl benzidine (TMB).
7. Color evidenced where Ab present.

This test evidences a proof of concept in that the ability of antibody to be displaced by unbound antibody in accordance with LeChatelier's principles of equilibrium. The ability of said unbound antigen or facsimile antigen to present changing concentration at the interface of the plate/film permits the unbound antigen to successfully compete for the binding sites occupied by the bound and conjugated antibody. The removal of color evidences this principle in action, thereby resulting in controllable areas of color or transparency being evidenced.

The antibody is in water soluble varnish (WSV) and antigen is bound to antibody with color indicator such that color forms with binding; upon exposure, bacteria having higher affinity competes out the color, and the color containing antigen is displaced into food.

Thus the displacement test goes from color (in this particular case, a blue color) to clear to show a difference in binding.

Figure 2:
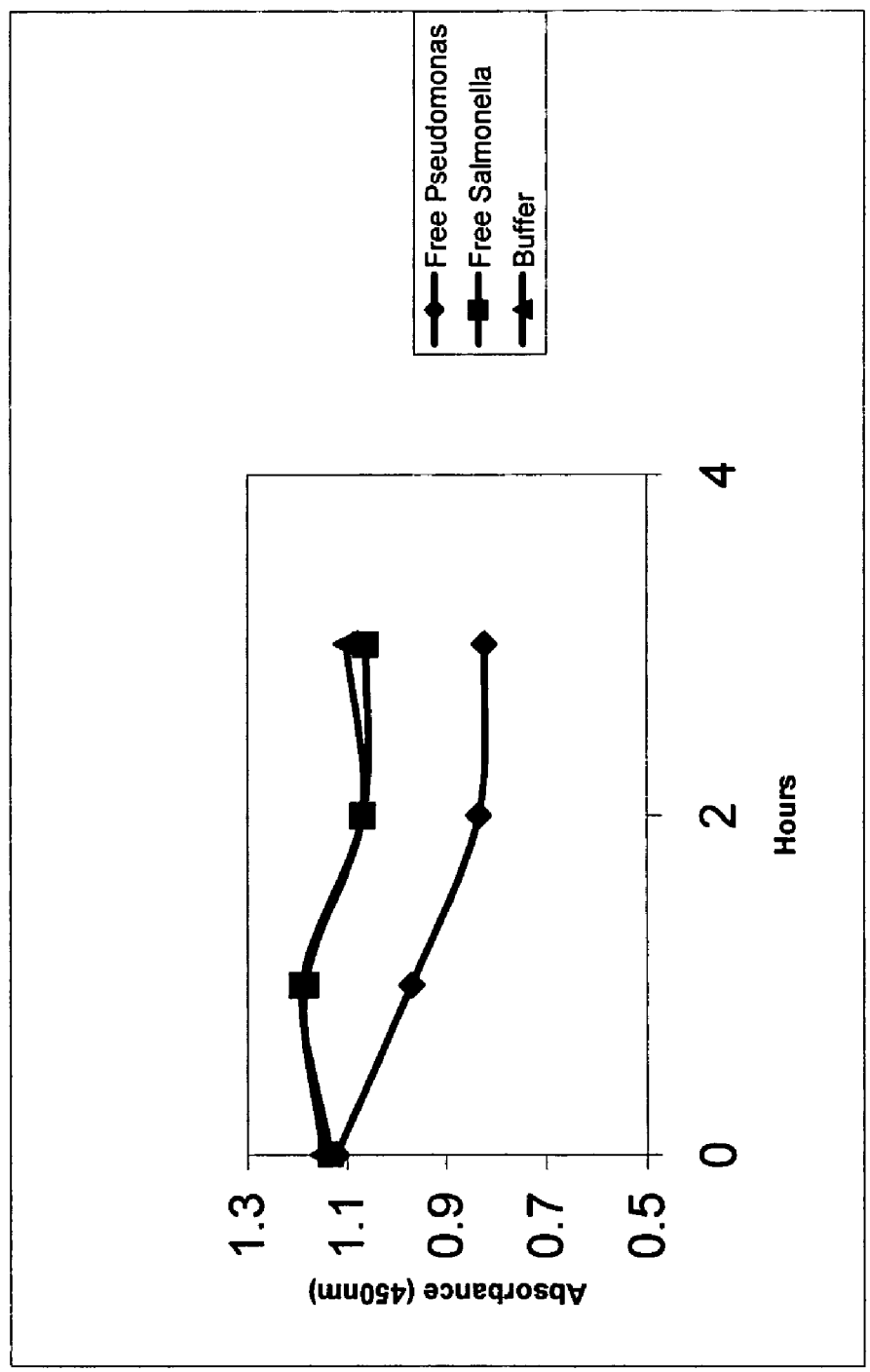
FIG. 2 is a graph demonstrating displacement of HRP-conjugated antibody from *Pseudomonas* specific lipopolysaccharide.

Now referring to FIG. 2, by utilizing antibody as the displaceable component, the conjugation of pigment in all assays is standardized, and the regulatory body required "leaching" tests are standardized, as the material most likely to be transferred to foodstuffs will be, in each assay, the conjugated antibody.

The graph in FIG. 2 demonstrates the displacement of HRP-conjugated antibody from *Pseudomonas* specific to lipopolysaccharide (LPS) coated on a polystyrene plate by free *Pseudomonas* in solution but not by non-specific bacteria (*Salmonella*) nor by the buffer solution.

Figure 3:
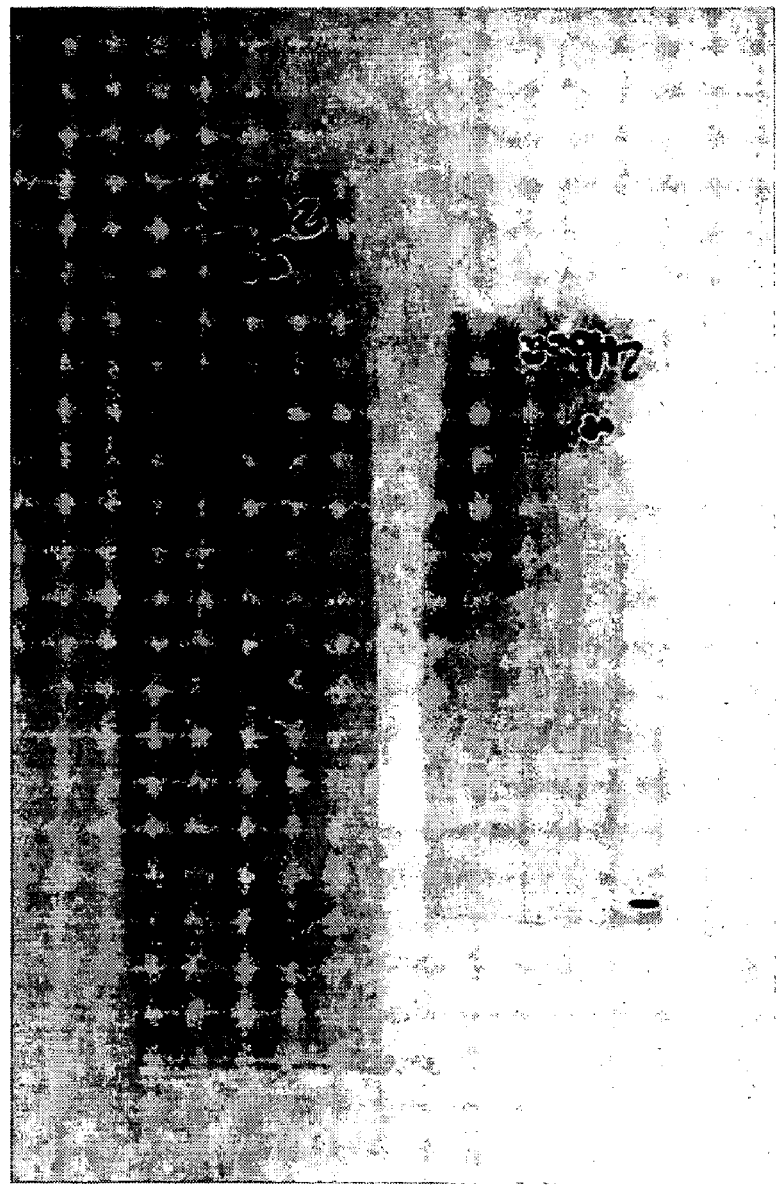
FIG. 3 is a photograph of a working assay

FIG. 3—Displacement on Film

Now referring to FIG. 3, *Pseudomonas* LPS was printed in an icon shape in a water based varnish on the XY plotter at a concentration of 1 mg/mL (not optimized).

The strips of plastic were placed in a 50 mL bath of 7-4 antibody-HRP conjugate for 1 hour at room temperature.

The strips were washed with wash buffer and placed in a 50 mL bath of either wash buffer (control) or heat-killed *Pseudomonas* solution.

The strips were then washed in wash buffer and allowed to dry.

TMB was added for 20 minutes at room temperature.

The results indicated that the 7-4 antibody-HRP conjugate was displaced by the *Pseudomonas* in solution, thereby again proving the displacement assay principle which is at the heart of the instant invention.

Illustrative of films which will function in the present invention is a film containing a structural polymer base having a treated surface and incorporating therein a fluorescing antibody receptor and finally a stabilized gel coat. These films may be untreated polyethylene or polyvinylchloride films which are amenable to antibody immobilization by various mechanisms, e.g. by adsorption. In a particular embodiment, the films may be first cleaned, e.g. by ultrasonication in an appropriate solvent, and subsequently dried. For example the polymer sheet may be exposed to a fifteen minute ultrasonic treatment in a solvent such as methylene chloride, acetone, distilled water, or the like. In some cases, a series of solvent treatments are performed. Subsequently the film is placed in a desiccating device and dried. Alternatively, these films may be created by first exposing the film to an electron discharge treatment at the surface thereof, then printing with a fluorescing antibody receptor. Subsequently, a drying or heating step may be utilized to treat the film to immobilize the receptor. Next, the film is washed to remove un-immobilized receptor; the film is then coated with a gel and finally dried.

Additional modifications to polyolefin films may be conducted to create the presence of functional groups, for example a polyethylene sheet may be halogenated by a free radical substitution mechanism, e.g. bromination, chlorosulfonation, chlorophosphorylation or the like. Furthermore, a halodialkylammonium salt in a sulfuric acid solution may be useful as a halogenating agent when enhanced surface selectivity is desirable.

Grafting techniques are also contemplated wherein hydrogen abstraction by transient free radicals or free radical equivalents generated in the vapor or gas phase is conducted. Grafting by various alternative means such as irradiation, various means of surface modification, polyolefin oxidation, acid etching, inclusion of chemical additive compounds to the polymer formulation which have the ability to modify the surface characteristics thereof, or equivalent techniques are all contemplated by this invention.

Additionally, the formation of oxygenated surface groups such as hydroxyl, carbonyl and carboxyl groups via a flame treatment surface modification technique is contemplated.

Further, functionalization without chain scission by carbene insertion chemistry is also contemplated as a means of polyolefin polymer modification.

Illustrative of the types of commercially available films which might be utilized are polyvinylchloride films and a straight polyethylene film with electron discharge treatment marketed under the trademark SCLAIR®. The electron discharge treatment, when utilized, renders the film much more susceptible to immobilization of the antibodies on its surface. Additional films which might be utilized are Nylon 66 films, for example DARTEK®, a coextrudable adhesive film such as BYNEL® and a blend of BYNEL® with polyethylene film.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A process for producing a displacement assay on a clear and flexible polymer film comprising the steps of:
    a) producing a heat-killed antigen or facsimile antigen;
    b) immobilizing said antigen or facsimile antigen upon a clear and flexible polymer film;
    c) binding a pigmented antibody to said antigen or facsimile antigen within a water soluble varnish; and
    d) washing away any unbound antigen or facsimile antigen;

wherein a presence of color evidences the presence of said pigmented antibody, and binding of a contaminant displaces said pigmented antibody, whereby an absence of color signals binding of the contaminant.

2. The process of claim 1 wherein said antibody is labeled with horseradish peroxidase.

3. The process of claim 1 further comprising a step of adding a color producing agent, wherein said color producing agent is tetramethyl benzidine (TMB).

* * * * *